US011073475B2

(12) United States Patent
Palassis et al.

(10) Patent No.: US 11,073,475 B2
(45) Date of Patent: Jul. 27, 2021

(54) OPTICAL NITRATE SENSOR FOR MULTIPARAMETER WATER QUALITY MEASUREMENT

(71) Applicant: YSI, INC., Yellow Springs, OH (US)

(72) Inventors: Christopher John Palassis, Yellow Springs, OH (US); Miguel A. Rojo, West Carrollton, OH (US)

(73) Assignee: YSI, INC., Yellow Springs, OH (US)

( * ) Notice: Subject to any disclaimer, the term of this patent is extended or adjusted under 35 U.S.C. 154(b) by 0 days.

(21) Appl. No.: 15/451,853

(22) Filed: Mar. 7, 2017

(65) Prior Publication Data

US 2017/0254752 A1 Sep. 7, 2017

Related U.S. Application Data

(60) Provisional application No. 62/304,678, filed on Mar. 7, 2016, provisional application No. 62/305,742, filed on Mar. 9, 2016.

(51) Int. Cl.
*G01N 21/59* (2006.01)
*G01N 33/18* (2006.01)
(Continued)

(52) U.S. Cl.
CPC ......... *G01N 21/59* (2013.01); *G01N 21/0303* (2013.01); *G01N 21/33* (2013.01);
(Continued)

(58) Field of Classification Search
CPC .... G01N 21/33; G01N 33/188; G01N 21/276; G01N 33/18; G01N 21/00; G01N 21/59;
(Continued)

(56) References Cited

U.S. PATENT DOCUMENTS 4,248,598 A  2/1981 Blunck
4,829,186 A  5/1989 McLachlan et al.
(Continued)

FOREIGN PATENT DOCUMENTS

AU  657477 B2  3/1995
CA  2589516 C  6/2006
(Continued)

OTHER PUBLICATIONS

Author: Michael S. Shur et al., Title: Deep-Ultraviolet Light-Emitting Diodes, Date: Jan. 2010, Publisher: IEEE Transactions on Electron Devices.*

(Continued)

*Primary Examiner* — Mark R Gaworecki
(74) *Attorney, Agent, or Firm* — Ware, Fressola, Maguire & Barber LLP (57) ABSTRACT

An optical nitrate sensor features a signal processor or signal processing module configured to: receive signaling containing information about a measurement (M) of UV optical absorbance of nitrate dissolved in water of a UV light that is generated by a UV LED centered at 229 nm and that traverses a confined volume of the water within a prescribed region of a sensor body, and also about a reference sample (R) of a portion of the UV light not traversing the confined volume of the water; and determine corresponding signaling containing information about the concentration of nitrate dissolved in the water, based upon the signaling received.

29 Claims, 8 Drawing Sheets

The Basic Signal Processing Functionality (51) Int. Cl.
 *G01N 21/03* (2006.01)
 *G01N 21/33* (2006.01)

(52) U.S. Cl.
 CPC ... *G01N 33/188* (2013.01); *G01N 2021/0307* (2013.01); *G01N 2201/062* (2013.01); *G01N 2201/0668* (2013.01); *G01N 2201/12* (2013.01)

(58) Field of Classification Search
 CPC ......... G01N 2201/129; G01N 33/0037; G01N 2201/062; G01N 2201/12; G01N 21/0303; G01N 2021/0307; G01N 2201/0668
 USPC ....................................................... 250/373
 See application file for complete search history.

(56) References Cited

U.S. PATENT DOCUMENTS

| | | | |
|---|---|---|---|
| 4,868,127 A | 9/1989 | Blades et al. | |
| 5,244,811 A | 9/1993 | Matthews | |
| 5,420,432 A | 5/1995 | Manook et al. | |
| 5,443,991 A | 8/1995 | Godec et al. | |
| 5,630,987 A * | 5/1997 | Briggs | G01N 21/276 422/82 |
| 5,680,209 A * | 10/1997 | Machler | G01J 3/02 250/373 |
| 5,864,140 A | 1/1999 | Owens et al. | |
| 6,007,777 A | 12/1999 | Purcell et al. | |
| 6,313,468 B1 | 11/2001 | Wedekamp | |
| 6,423,249 B1 | 7/2002 | Leveille | |
| 6,444,474 B1 | 9/2002 | Thomas et al. | |
| 6,451,613 B1 | 9/2002 | Blades et al. | |
| 6,734,021 B1 | 5/2004 | Saito et al. | |
| 6,737,276 B1 | 5/2004 | Voss et al. | |
| 7,598,086 B2 | 10/2009 | Zhao | |
| 7,655,473 B2 * | 2/2010 | Golitz | G01N 21/33 436/110 |
| 8,557,597 B2 | 10/2013 | Akechi et al. | |
| 8,663,561 B2 | 3/2014 | Patton | |
| 8,835,875 B2 | 9/2014 | She et al. | |
| 8,957,387 B2 | 2/2015 | Sexton et al. | |
| 8,981,314 B2 | 3/2015 | Klinkhammer et al. | |
| 9,255,878 B2 * | 2/2016 | Preiner | G01N 33/24 |
| 9,588,050 B2 * | 3/2017 | Yahata | G01N 21/75 |
| 2002/0117639 A1 * | 8/2002 | Paolini | G01N 21/8483 250/559.1 |
| 2002/0160517 A1 * | 10/2002 | Modzelewski | G01N 21/8483 436/44 |
| 2004/0043499 A1 | 3/2004 | Lee-Alvarez | |
| 2004/0130397 A1 * | 7/2004 | Mactaggart | H03F 3/08 330/308 |
| 2006/0079740 A1 * | 4/2006 | Silver | A61B 5/6882 600/309 |
| 2006/0091319 A1 | 5/2006 | Steuerwald et al. | |
| 2009/0103082 A1 * | 4/2009 | Black | G01N 15/1463 356/301 |
| 2009/0158819 A1 * | 6/2009 | Vincent | G01N 33/1886 73/61.43 |
| 2009/0166520 A1 * | 7/2009 | Tuli | G01V 9/00 250/253 |
| 2010/0159601 A1 * | 6/2010 | Patton | G01N 35/08 436/43 |
| 2010/0261280 A1 * | 10/2010 | Black | G01N 15/1463 436/50 |
| 2010/0330690 A1 * | 12/2010 | Kimoto | G01N 1/2205 436/163 |
| 2011/0066009 A1 * | 3/2011 | Moon | A61B 5/0205 600/301 |
| 2011/0242530 A1 * | 10/2011 | Tuli | G01V 9/00 356/300 |
| 2012/0135531 A1 * | 5/2012 | Silver | A61B 5/0205 436/116 |
| 2013/0202721 A1 * | 8/2013 | Silver | A61B 5/413 424/718 |
| 2013/0258317 A1 * | 10/2013 | Preiner | G01N 21/33 356/51 |
| 2015/0127271 A1 * | 5/2015 | Liu | G01N 35/00871 702/32 |
| 2015/0230742 A1 * | 8/2015 | Silver | A61B 5/0205 600/348 |
| 2015/0362476 A1 | 12/2015 | Clements et al. | |
| 2016/0024552 A1 * | 1/2016 | Reardon | C12Y 114/13 435/25 |
| 2016/0054228 A1 | 2/2016 | Yahata et al. | |
| 2016/0054281 A1 * | 2/2016 | Smeeton | G01N 21/3103 250/373 |

FOREIGN PATENT DOCUMENTS

| | | |
|---|---|---|
| CN | 1148173 A | 4/1997 |
| CN | 102042963 A | 5/2011 |
| DE | 2810117 A1 | 9/1979 |
| DE | 3223167 A1 | 12/1983 |
| DE | 3324606 A1 | 1/1985 |
| DE | 19500803 A1 | 12/1995 |
| DE | 19902396 A1 | 8/2000 |
| DE | 19947940 A1 | 5/2001 |
| DE | 10228929 A1 | 1/2004 |
| DE | 102007026717 A1 | 12/2008 |
| DE | 102008028058 A1 | 12/2009 |
| DE | 202015000747 U1 | 4/2015 |
| EP | 0039088 A1 | 11/1981 |
| EP | 0682250 A1 | 11/1995 |
| EP | 0738887 A1 | 10/1996 |
| EP | 0823054 A1 | 2/1998 |
| GB | 2 312 278 A | 10/1997 |
| JP | 2006194775 A | 7/2006 |
| WO | 9803855 A1 | 1/1998 |
| WO | 2010051842 A1 | 5/2010 |

OTHER PUBLICATIONS

Korostynska, O., A. Mason, and A. I. Al-Shamma'a. "Monitoring of nitrates and phosphates in wastewater: current technologies and further challenges." International journal on smart sensing and intelligent systems, vol. 5.1, Mar. 1, 2012. (pp. 149-176) http://www-ist.massey.ac.nz/s2is/issues/v5/n1/papers/paper9.pdf.

Cleary, John, Damien Maher, and Dermot Diamond. "Development and deployment of a microfluidic platform for water duality monitoring." Smart Sensors for Real-Time Water Quality Monitoring. Springer Berlin Heidelberg, published Jan. 2013, printed Mar. 25, 2016. (pp. 125-148) http://doras.dcu.ie/18122/1/Chapter_20130110_Development_and_deployment_of_a_microfluidic_platform.pdf.

Bridgeman, Jonathan, et al. "Portable LED fluorescence instrumentation for the rapid assessment of potable water quality." Science of the Total Environment 524, Apr. 2015. (pp. 338-346) https://www.researchgate.net/profile/Andy_Baker4/publication/275366885_Portable_LED_fluorescence_instrumentation_for_the_rapid_assessment_of_potable_water_quality/links/554423590cf23ft716853b41.pdf.

Younos, Tamim, and Christopher J. Heyer. The Handbook of Environmental Chemistry 33, including pp. 1 to 292, having a section entitled "Advances in Water Sensor Technologies and Real-Time Water Monitoring." Advances in Watershed Science and Assessment. Springer International Publishing, 2015. (pp. 171-203) http://www.dnulib.edu.vn:8080/dspace/bitstream/DNULIB_52011/6405/1/advances_in_watershed_science_and_assessment.pdf#page=186.

Moore, Casey, et al. "Optical tools for ocean monitoring and research", 2009. http://darchive.mblwhoilibrary.org/bitstream/handle/1912/3098/os-5-661-2009.pdf?sequence=1&isAllowed=y.

English language Abstract for CN102042963.
English language Abstract for DE3223167.
English language Abstract for DE3324606.
English language Abstract for DE10228929.
English language Abstract for DE19500803.

(56) References Cited

OTHER PUBLICATIONS

English language Abstract for DE19902396.
English language Abstract for DE19947940.
English language Abstract for DE102007026717.
English language Abstract for DE102008028058.
English language Abstract for EP0682250.
English language Abstract for EP0823054.
Interactive Geospatial Analysis Tool for Estimating Watershed-Scale Consumptive Use: Potomac River Basin Case Study, published 2015.
Ultra Setter: A Pressure Independent Control Valve That Maintains 100% Authority At All Times—A Real Energy Saver, published Apr. 2015.
Deep UV Light Emitting Diodes, printed Jun. 29, 2016.
English language Abstract of EP0039088.
English language Abstract of DE2810117.
English language translation of application with an Abstract of JP2006194775.
English language Abstract for CN1148173A, not available. Abstract of corresponding English language EP073887.
English language Abstract of EP073887.
Ianoul, et al., "UV Resonance Raman Spectroscopic Detection of Nitrate and Nitrite in Wastewater Treatment Processes", Analytical Chemistry, 2002, vol. 74, printed on May 15, 2017. (pp. 1458-1461).
English language Abstract of DE202015000747.

\* cited by examiner

Apparatus 10

Signal processor or processing module 12 configured at least to:

receive signaling $S_{in}$ containing information about a measurement (M) of UV optical absorbance of nitrate dissolved in water of a UV light that is generated by a UV LED centered at 229nm and that traverses a confined volume of the water within a prescribed region of a sensor body, and also about a reference sample (R) of a portion of the UV light not traversing the confined volume of the water;

determine corresponding signaling $S_{out}$ containing information about the concentration of nitrate dissolved in the water, based upon the signaling received; and/or provide the corresponding signaling $S_{out}$ containing information about the concentration of nitrate dissolved in the water.

Other signal processor circuits or components 14 that do not form part of the underlying invention, e.g., including input/output modules, one or more memory modules, data, address and control busing architecture, etc.

$S_{in}$  $S_{out}$

*FIG. 1A:* The Basic Signal Processing Functionality

20

20a, Receive signaling $S_{in}$ containing information about a measurement (M) of UV optical absorbance of nitrate dissolved in water of a UV light that is generated by a UV LED centered at 229nm and that traverses a confined volume of the water within a prescribed region of a sensor body, and also about a reference sample (R) of a portion of the UV light not traversing the confined volume of the water

20b, Determine corresponding signaling $S_{out}$ containing information about the concentration of nitrate dissolved in the water, based upon the signaling received

20c, Provide corresponding signaling $S_{out}$ containing information about the concentration of nitrate dissolved in the water

*FIG. 1B:* The Basic Method

*FIG. 2:* Model of the optical interaction of components, including where a portion of light Lr is sampled from the UV LED before interacting with the sample volume.

FIG. 3: Graph showing apparatus performance and linearity plot from 1-10 ppm NO3 - N

FIG. 4: Optical sensing using a light pipe concept

*FIG. 5:* Optical sensing using a cell spacer

*FIG. 6:* Optical sensing using a variable cell

*FIG. 7C:* Section A-A in FIG. 7A    *FIG. 7D:* Section B-B in FIG. 7B

*FIG. 7:* Absorbence Module Concept

FIG. 9: Optical sensing utilizing a quartz tube to define the optical path of 1cm

*FIG. 10:* Groomable sensor concept, including where a sonde's central wiper W sweeps thru a measurement cell MC to keep it clear from biofouling

OPTICAL NITRATE SENSOR FOR MULTIPARAMETER WATER QUALITY MEASUREMENT

CROSS-REFERENCE TO RELATED APPLICATIONS

This application claims benefit to provisional patent application Ser. No. 62/304,678 (911-023.3-1//N-YSI-0033), filed 7 Mar. 2016, as well as a companion patent application Ser. No. 62/305,742 (911-023.4-1//N-YSI-0034), filed 9 Mar. 2016, which are both incorporated by reference in their entirety.

BACKGROUND OF THE INVENTION

1. Field of Invention

This invention relates to a technique for determining the quality of water; and more particularly relates to a technique for determining the quality of water using an optical sensor for multiparameter water quality monitoring.

2. Description of Related Art

Eutrophication is understood to be an excessive richness of nutrients in a lake or other body of water, frequently due to runoff from the land, which causes a dense growth of plant life and death of animal life from lack of oxygen. Eutrophication due to such nutrient loading of such environmental water is one of the biggest challenges to aquatic health today. Nitrate detection in such environmental water is essential to help solve these problems. Current sensors available in the market are not amenable to long term monitoring due to reagent consumption (wet chemistry systems) or excessive power consumption (spectrometer-based systems). In view of this, as demand grows to reduce nutrient loading, there is a need in the art for a environmental water sensor that is part of a long-term monitoring, multi-parameter sensing suite.

SUMMARY OF THE INVENTION

The Underlying Technique in General

By way of example, the present invention provides new and unique techniques for determining the quality of water using an optical sensor for multiparameter water quality monitoring, e.g., to solve the aforementioned need in the art.

By way of example, and according to some embodiment, the present invention provides apparatus, e.g., in the form of a multiparameter sonde-based sensor, that measures ultraviolet (UV) absorbance of nitrate at ~229 nm (nanometers) that utilizes deep UV light emitting diodes (LEDs) and that leverages other sensors in the payload to achieve a fully compensated nitrate measurement. This sensor would have the capability to operate on battery power and be deployed in environmental water for long-term nitrate monitoring as part of a payload of water quality monitoring sensors.

Optical absorbance is a measure of light intensity attenuation, relative to a reference measurement, over a fixed distance. Nitrate dissolved in water has a well-known optical absorbance in the UV spectrum in a range from 200 nm-230 nm. Recent advances in LED technology have allowed access to the weak optical absorbance in the 229 nm range. This weak optical absorbance is sufficient to measure nitrate concentrations typical in freshwater systems of 1-10 ppm (i.e., parts per million).

To make this measurement, a UV LED, centered at 229 nm, may be configured to illuminate water confined within a prescribed region of the sensor body. Light traversing the confined volume or water is attenuated in the presence of an absorbing species. The attenuated light impinges onto a photodiode where a photocurrent is generated and is subsequently converted into a voltage via a transimpedance amplifier. This signal is designated as the measurement (M) or the measurement signal. Prior to interacting with the sample, a portion of the UV light is sampled via a reference photodiode where the photocurrent is converted into a voltage via a transimpedance amplifier without interacting with the water. This signal is designated as the reference (R) or the reference signal.

The absorbance can be calculated as follows:

$$\text{Absorbance} = -\log(\text{optical transmittance}) = -\log(M/aR),$$

where a is a proportionality constant that can be adjusted for electrical gain normalization

Methods of Injecting Light and Receiving the Optical Signal

1. Ultraviolet light can be directly presented to the water along a prescribed path. In this case light emitted from the LED is unencumbered by additional optics. Light traversing the gap directly impinges upon a 229 nm-filtered photodiode.
2. Ultraviolet light can be presented to the water via an optical waveguide of suitable material (e.g., typically a sapphire or a UV grade fused silica). This removes the necessity of the LED to be located near the point of measurement. The advantage of separating the LED from the optical detector is that electrical noise is minimized by physically separating susceptible components.
3. Light traversing the prescribed optical path impinges onto a photodiode where the light is converted into an electrical current. Light can directly couple to the photodiode without any additional optical elements or light can be captured by an optical waveguide of suitable material (e.g., a sapphire or a UV grade fused silica) and then channeled to a photodiode, extended from the point of measurement.

Variable Path Length

Variation of nitrate concentration in natural water can range from a few parts per billion to tens of parts per million. While absorbance can be measured as an attenuation as shown above, it is truly based on the concentration of an absorbing species, the interaction length with the absorbing species, and the molar absorptivity which varies with wavelength of light used. This is described by Beer's Law as Absorbance=$\varepsilon$lc; where $\varepsilon$=molar absorptivity, c=analyte concentration, and l=interaction length. This implies for optimized signal contrast, a long interaction length is needed for the lowest concentrations, and a short interaction length is needed for high concentrations. Incorporating the ability to vary the optical path length would allow for sensor optimization for the concentration range of interest. Varying the optical path can be accomplished in several ways. Consider a sensor with a measurement volume of a U-shape of a fixed length. Light propagates across the volume from light source to detector. For high concentration applications the signal attenuation may be too high therefore it may be advantageous to shorten the interaction length between the light and the water. This can be accomplished by inserting an optically transparent spacer in the cell such as a sapphire or fused silica rod. The interaction length then becomes the difference between the original cell length and the spacer length. Another method for varying the cell length physically changes the distance between the source and detector rather than inserting a spacer.

Examples of Particular Embodiments

According to some embodiments, the present invention may include apparatus, featuring a signal processor or signal processing module configured to:

receive signaling containing information about a measurement (M) of UV optical absorbance of nitrate dissolved in water of a UV light that is generated by a UV LED centered at 229 nm and that traverses a confined volume of the water within a prescribed region of a sensor body, and also about a reference sample (R) of a portion of the UV light not traversing the confined volume of the water; and determine corresponding signaling containing information about the concentration of nitrate dissolved in the water, based upon the signaling received.

The apparatus may include one or more of the following additional features:

The apparatus may include, or take the form of, an optical nitrate sensor, e.g., including the sensor having the prescribed region.

The signal processor or signal processing module may be configured to provide the corresponding signaling containing information about the concentration of nitrate dissolved in the water.

The signal processor or signal processing module may be configured to determine the measurement of the UV optical absorbance based upon the following equation:

$$\text{Absorbance}=-\log(\text{optical transmittance})=-\log(M/aR),$$

where a is a proportionality constant that can be adjusted for electrical gain normalization.

The signaling may contain information about the measurement (M) measured and received from a measurement photodiode, where a photocurrent is generated and is subsequently converted into a voltage via a transimpedance amplifier.

The signaling may contain information about the reference sample (R) measured and received from a reference photodiode, where a photocurrent is generated and is subsequently converted into a voltage via a transimpedance amplifier.

The UV light may traverse the confined volume of the water over a varying path length that depends on a concentration range of interest for the nitrate concentration determined.

The apparatus may include the sensor body configured with a path length of the confined volume of the water within the prescribed region.

The sensor body may include a cell spacer configured within part of the path length.

The sensor body may include a variable cell configured to be adapted with a first path length for determining high concentrations of nitrate dissolved in the water, or with a second path length for determining low concentrations of nitrate dissolved in the water, including where the first path is shorter than the second path.

The sensor may include, or take the form of, a multiparameter sonde-based sensor.

The prescribed region of the sensor body may include a sampling chamber for containing the water.

The apparatus may include a quartz tube, and the prescribed region of the sensor body forms part of the quartz tube.

The sampling chamber may include, or take the form of, a two-part construction having a first sub-chamber and a second sub-chamber. The first sub-chamber may include a first sub-chamber extension; the second sub-chamber may include a second sub-chamber extension; and the first sub-chamber extension and the second sub-chamber extension may be configured to form either a first path for a high concentration measurement or a second path for a low concentration measurement. The first path for the high concentration measurement is shorter than the second path for the low concentration measurement. The first sub-chamber extension and the second sub-chamber extension may be coupled together and configured with an O-ring seal inbetween. The first sub-chamber extension and the second sub-chamber extension may be slidably coupled together.

The prescribed region may include a sampling chamber; and the apparatus may include a UV LED configured on one side of the sampling chamber, and a combination of a filter and measurement photodiode configured on the other side of the sampling chamber. The apparatus may also include one or more light pipes, each configured to channel light to or from the sampling chamber.

The apparatus may include a photodiode replacement module having a plug, a diode housing and a measurement diode arranged therein.

The apparatus may include an LED replacement module having a UV LED and a reference photodiode.

By way of example, the signal processor or signal processor module may include, or take the form of, some combination of a signal processor and at least one memory including a computer program code, where the signal processor and at least one memory are configured to cause the apparatus to implement the functionality of the present invention, e.g., to respond to signaling received and to determine the corresponding signaling, based upon the signaling received.

According to some embodiments, the present invention may include a method featuring steps for receiving in a signal processor or processing module signaling containing information about a measurement (M) of UV optical absorbance of nitrate dissolved in water of a UV light that is generated by a UV LED centered at 229 nm and that traverses a confined volume of the water within a prescribed region of a sensor body, and also about a reference sample (R) of a portion of the UV light not traversing the confined volume of the water; and determining in the signal processor or processing module corresponding signaling containing information about the concentration of nitrate dissolved in the water, based upon the signaling received.

The method may also include one or more of the features set forth above.

BRIEF DESCRIPTION OF THE DRAWING

The drawing, which are not necessarily drawn to scale, includes FIGS. 1-10, as follows:

FIG. 7 includes FIGS. 7A, 7B, 7C and 7D, showing a cell spacer concept based upon an absorbance module concept, according to some embodiments of the present invention, where

To reduce clutter in the drawing, each Figure does not include every reference label for every element shown therein.

DETAILED DESCRIPTION OF BEST MODE OF THE INVENTION

Figure 1A:
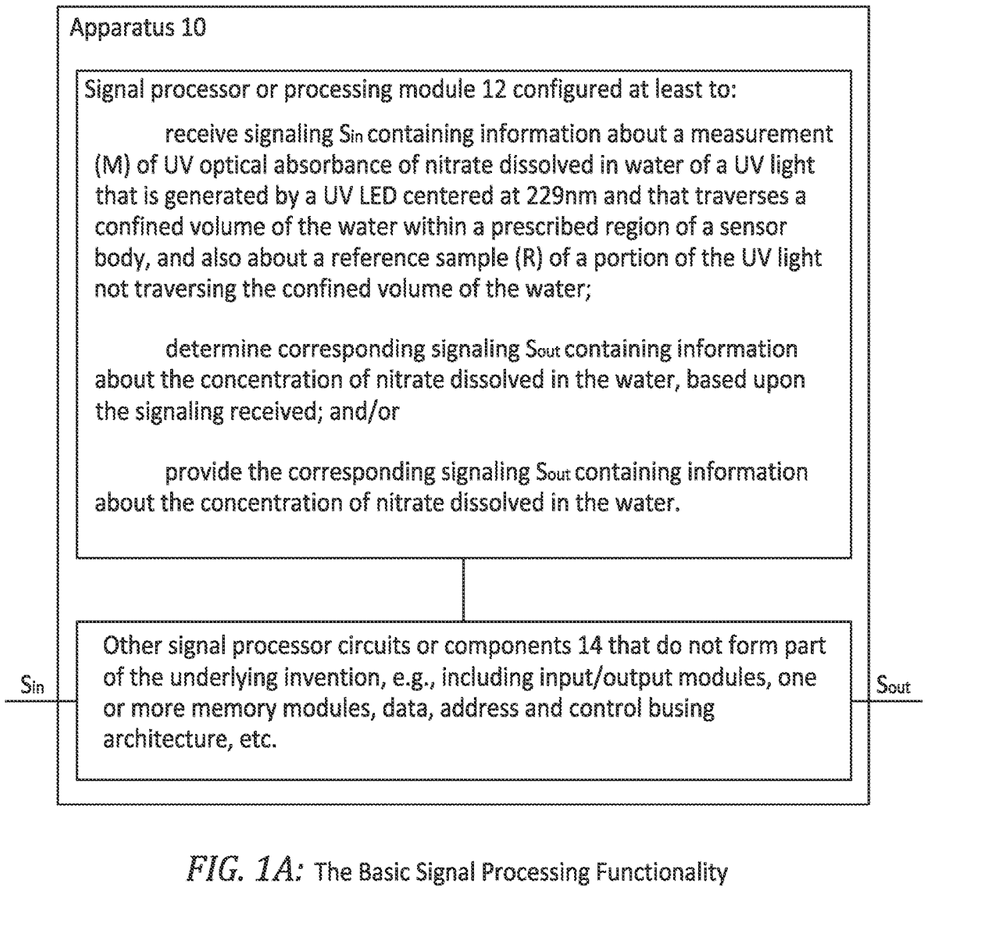
FIG. 1A shows a block diagram of apparatus, e.g., having a signal processor or signal processing module for implementing signal processing functionality, according to some embodiments of the present invention.

FIG. 1A: Implementation of Signal Processing Functionality

By way of further example, FIG. 1A shows apparatus 10 (e.g., an optical nitrate sensor) according to some embodiments of the present invention for implementing the associated signal processing functionality. The apparatus 10 may include a signal processor or processing module 12 configured at least to:
  receive signaling containing information about a measurement (M) of UV optical absorbance of nitrate dissolved in water of a UV light that is generated by a UV LED centered at 229 nm and that traverses a confined volume of the water within a prescribed region of a sensor body, and also about a reference sample (R) of a portion of the UV light not traversing the confined volume of the water; and
  determine corresponding signaling containing information about the concentration of nitrate dissolved in the water, based upon the signaling received.

In operation, the signal processor or processing module 12 may be configured to provide the corresponding signaling containing information about the concentration of nitrate dissolved in the water, e.g., for further processing, consistent with that set forth herein. The scope of the invention is not intended to be limited to any particular type, kind or manner of further processing, and may include further processing techniques either now known or later developed in the future.

By way of example, the functionality of the signal processor or processing module 12 may be implemented using hardware, software, firmware, or a combination thereof. In a typical software implementation, the signal processor or processing module 12 would include one or more microprocessor-based architectures having, e. g., at least one signal processor or microprocessor like element 12. One skilled in the art would be able to program with suitable program code such a microcontroller-based, or microprocessor-based, implementation to perform the signal processing functionality disclosed herein without undue experimentation. For example, the signal processor or processing module 12 may be configured, e.g., by one skilled in the art without undue experimentation, to receive the signaling containing information about a measurement (M) of UV optical absorbance of nitrate dissolved in water of a UV light that is generated by a UV LED centered at 229 nm and that traverses a confined volume of the water within a prescribed region of a sensor body, and also about a reference sample (R) of a portion of the UV light not traversing the confined volume of the water, consistent with that disclosed herein.

Moreover, the signal processor or processing module 12 may be configured, e.g., by one skilled in the art without undue experimentation, to determine the corresponding signaling containing information about the concentration of nitrate dissolved in the water, e.g., consistent with that disclosed herein. By way of example, the scope of the invention is not intended to be limited to any particular type or kind of signal processing implementation and/or technique for making the determination about the concentration of nitrate dissolved in the water, based upon the signaling received.

The scope of the invention is not intended to be limited to any particular implementation using technology either now known or later developed in the future. The scope of the invention is intended to include implementing the functionality of the signal processor(s) 12 as stand-alone processor, signal processor, or signal processor module, as well as separate processor or processor modules, as well as some combination thereof.

The apparatus 10 may also include, e.g., other signal processor circuits or components generally indicated 14, including random access memory or memory module (RAM) and/or read only memory (ROM), input/output devices and control, and data and address buses connecting the same, and/or at least one input processor and at least one output processor, e.g., which would be appreciate by one skilled in the art.

Figure 1B:
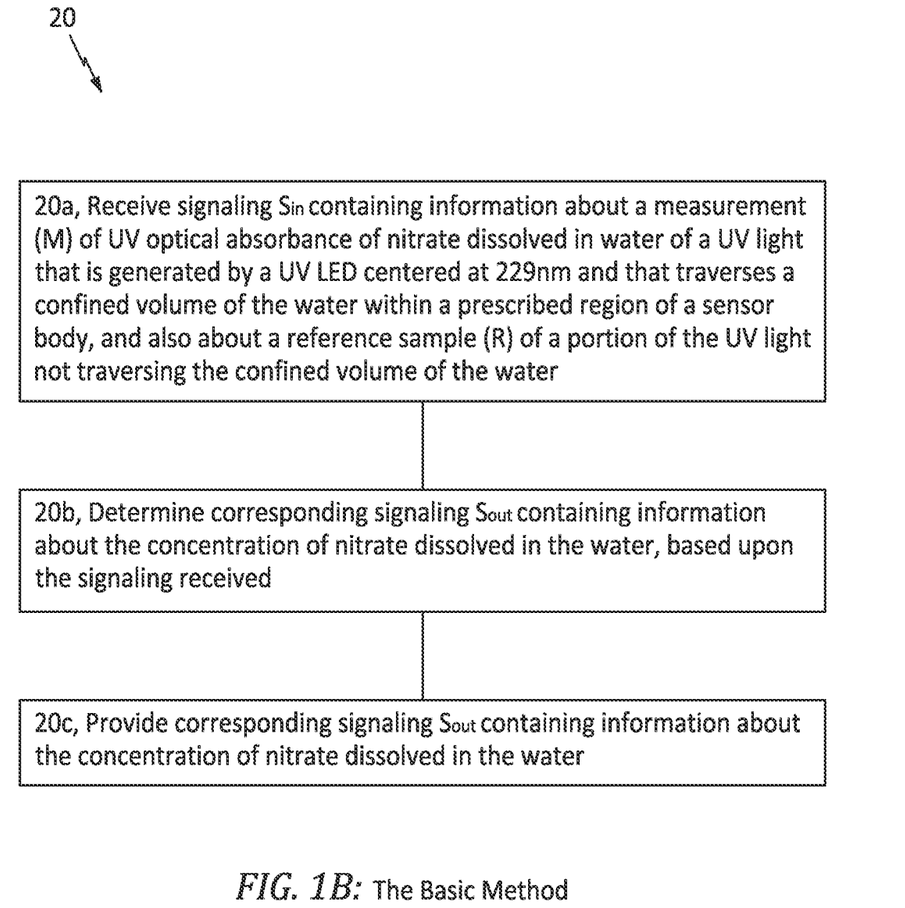
FIG. 1B shows a block diagram of a flow chart having steps for implementing a method, according to some embodiments of the present invention.

FIG. 1B: The Basic Method

According to some embodiments, the present invention may also include a method generally indicated as 20 comprising steps 20a, 20b and 20c, as follows:
  a step 20a for receiving in a signal processor or processing module like element 12 signaling containing information about a measurement (M) of UV optical absorbance of nitrate dissolved in water of a UV light that is generated by a UV LED centered at 229 nm and that traverses a confined volume of the water within a prescribed region of a sensor body, and also about a reference sample (R) of a portion of the UV light not traversing the confined volume of the water; and a step 20b for determining in the signal processor or processing module like element 12 corresponding signaling containing information about the concentration of nitrate dissolved in the water, based upon the signaling received.

The method may also include one or more of the features set forth above, including a step 20c for providing the corresponding signaling containing information about the concentration of nitrate dissolved in the water.

Figure 2:
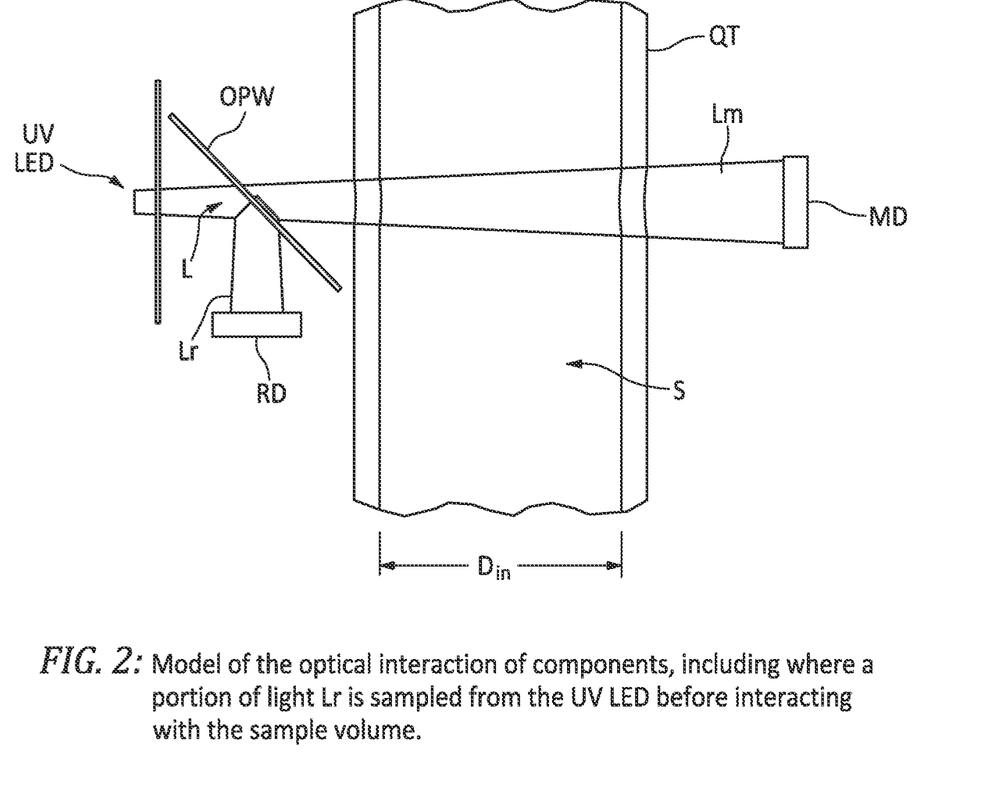
FIG. 2 shows a model of optical interaction of a prototype, including where a portion of light is sampled from the UV LED before interacting with the sample volume, according to some embodiments of the present invention.
Figure 3:
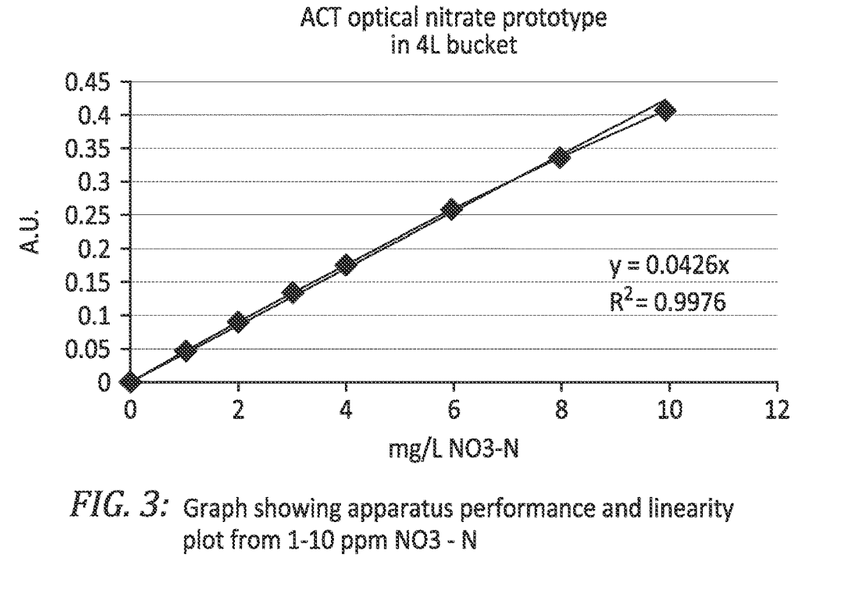
FIG. 3 is a graph of A.U. versus mg/l NO3-N showing a prototype performance and linearity plot from 1-10 ppm NO3-N, e.g., for an ACT optical nitrate portotype in a 4 L bucket.

FIG. 2

By way of example, FIG. 2 shows a model of optical interaction of a prototype, including where a portion of light is sampled from the UV LED before interacting with the sample volume. FIG. 2 is an optical ray trace diagram that shows UV light L propagating from left to right. A portion of light Lr is sampled by an optical pickoff window OPW (also known or referred to herein as an "optical sampling window") and reflected to a reference diode RD. The remaining light Lm interacts with a water sample S contained within a quartz tube QT that is used as a sample chamber and has a known inner diameter $D_{in}$ before impinging on a measurement photodiode MD.

Figures 4, 4C:
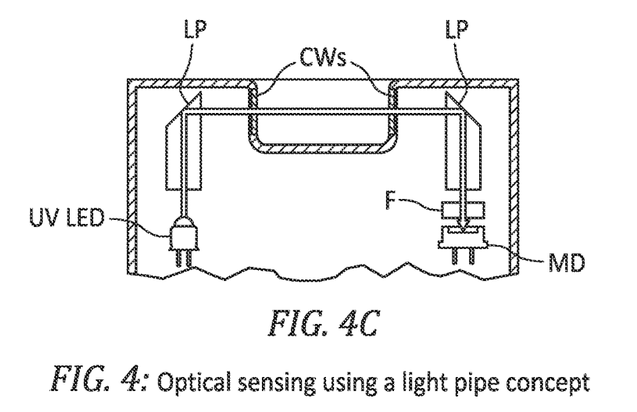
FIG. 4 includes FIGS. 4A, 4B and 4C, showing optical sensing techniques using a light pipe concept, according to some embodiments of the present invention.

FIG. 4: Optical Sensing Using Light Pipe(s)

FIG. 4 shows optical sensing techniques using a light pipe concept, according to some embodiments of the present invention.

Figure 4A:
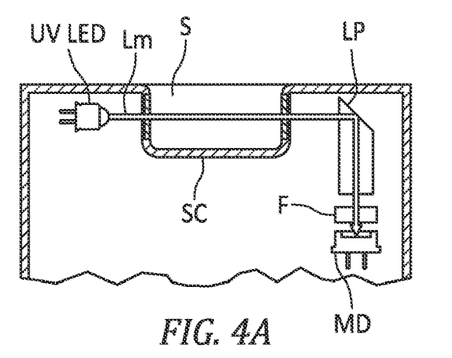

FIG. 4A shows a first optical sensing technique using a first light pipe concept, e.g. where the remaining light Lm provided from a UV LED arranged on one side of a sample chamber SC interacts with the water sample S contained within the sample chamber SC, passes through a light pipe LP arranged on the other side of the sample chamber SC, passes through a filter F and impinges on the measurement photodiode MD.

Figure 4B:
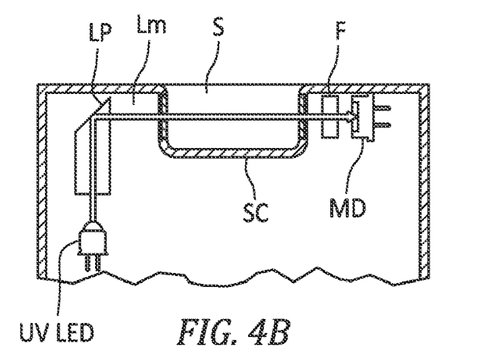

FIG. 4B shows a second optical sensing technique using a second light pipe concept, e.g. where the remaining light Lm provided from a light pipe LP arranged on one side of a sample chamber SC interacts with the water sample S contained within the sample chamber SC, passes through a filter F passes arranged on the other side of the sample chamber SC, and impinges on the measurement photodiode MD.

FIG. 4C shows a third optical sensing technique using a third light pipe concept, e.g. where the remaining light Lm provided from a first one of two light pipes LPs arranged on one side of a sample chamber SC interacts with the water sample S contained within the sample chamber SC, passes through a second one of two light pipes LPs arranged on the other side of the sample chamber SC, passes through a filter F and impinges on the measurement photodiode MD.

FIG. 4 does not show the portion of light Lr that is sampled by an optical pickoff window OPW and reflected to a reference diode RD, e.g., as shown in FIG. 2. FIG. 4C includes reference label CWs designating chamber windows for allowing light to pass into and from the sampling chamber SC.

FIG. 5: Optical Sensing Using Cell Spacer

FIG. 5 shows optical sensing techniques using a cell spacer concept, according to some embodiments of the present invention. In this optical sensing technique, a sapphire or UV grade fused silica rod R may be used to configured the path length, e.g., depending if low or high concentration measurement is needed.

Figure 5A:
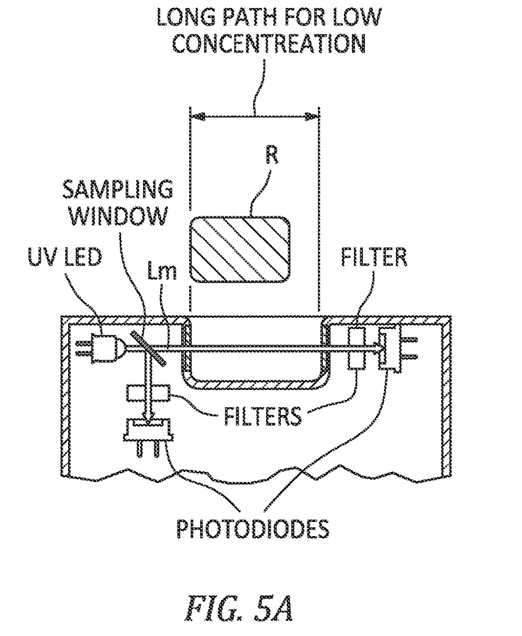
FIG. 5 includes FIGS. 5A and 5B, showing optical sensing techniques using a cell spacer concept, according to some embodiments of the present invention.

For example, FIG. 5A shows a first optical sensing technique using a first cell spacer concept, e.g. where the remaining light Lm provided from a sampling window SW arranged on one side of a sample chamber SC interacts with the water sample S contained within the sample chamber SC that does not have a sapphire or UV grade fused silica rod R configured therein, passes through a filter F passes arranged on the other side of the sample chamber SC, and impinges on the measurement photodiode MD. In this case, since a long path for a low concentration measurement is needed, then no sapphire or UV grade fused silica rod R may be used to configured the path length for the low concentration measurement.

Figure 5B:
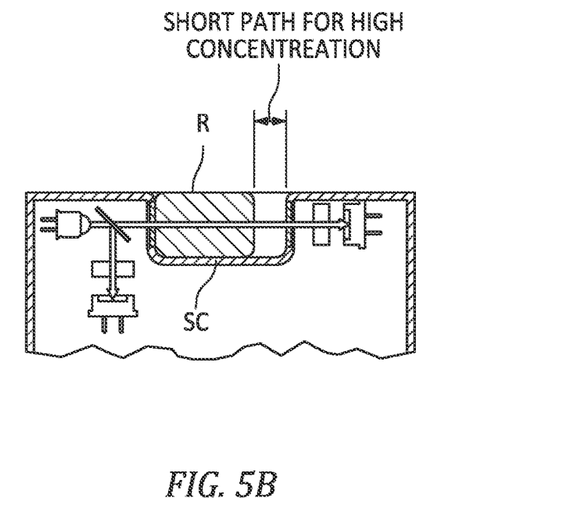

By way of further example, and in contrast to that shown in FIG. 5A, FIG. 5B shows a second optical sensing technique using a second cell spacer concept, e.g. where the remaining light Lm provided from a sampling window SW arranged on one side of a sample chamber SC interacts with the water sample S contained within the sample chamber SC that has a sapphire or UV grade fused silica rod R configured therein, passes through a filter F passes arranged on the other side of the sample chamber SC, and impinges on the measurement photodiode MD. In this case, since a short path for a high concentration measurement is needed, then the sapphire or UV grade fused silica rod R may be used to configured the path length for the high concentration measurement.

In contrast to that shown in FIG. 4, FIG. 5 shows the portion of light Lr that is sampled by a sampling window and reflected to a reference diode, e.g., like that shown in FIG. 2.

FIG. 6: Optical Sensing Using Variable Cell Spacer

FIG. 6 shows optical sensing techniques using a variable cell concept, according to some embodiments of the present invention. In this optical sensing technique, the sample chamber may be configured as a two-part construction having a first sub-chamber part SC1 and a second sub-chamber part SC2 that may be configured and adapted to vary the path length of the sample chamber SC, e.g., depending if a low or high concentration measurement is needed.

Figures 6A, 6B:
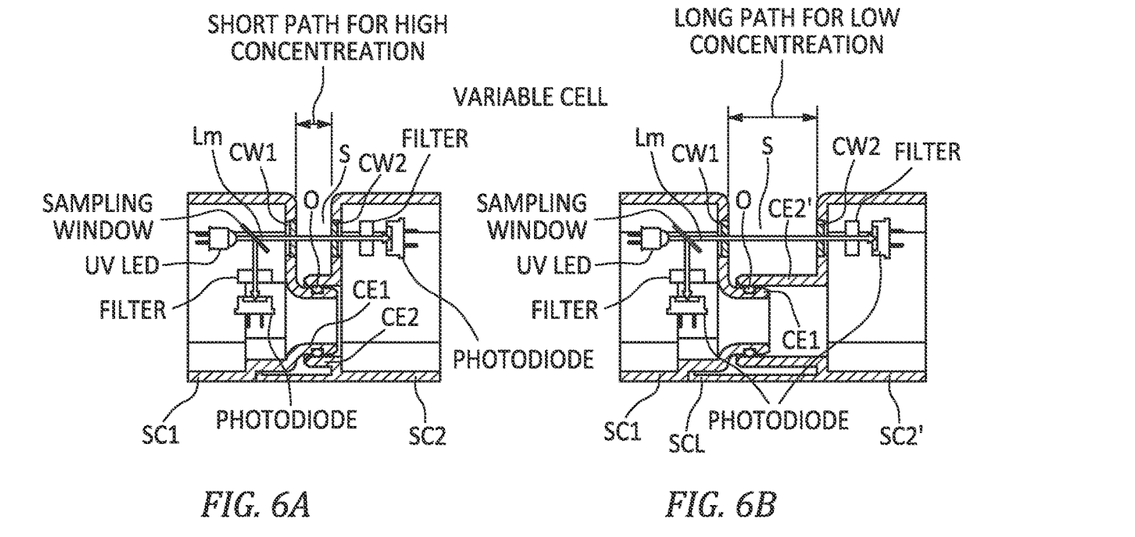
FIG. 6 includes FIGS. 6A and 6B, showing optical sensing techniques using a variable cell concept, according to some embodiments of the present invention.
Figure 7A:
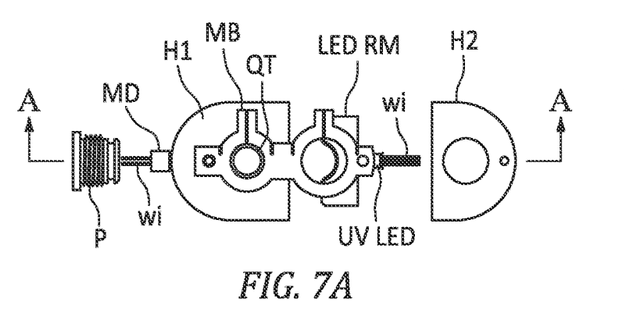
FIG. 7A is an exploded view of the cell spacer; where
Figure 7B:
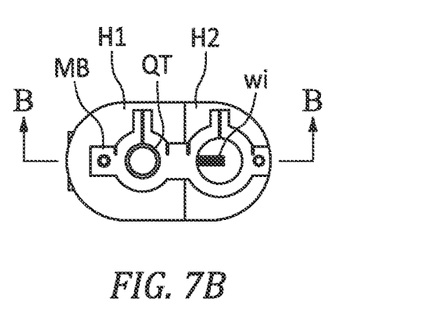
FIG. 7B is a view of the cell spacer when assembled; where
Figure 7C:
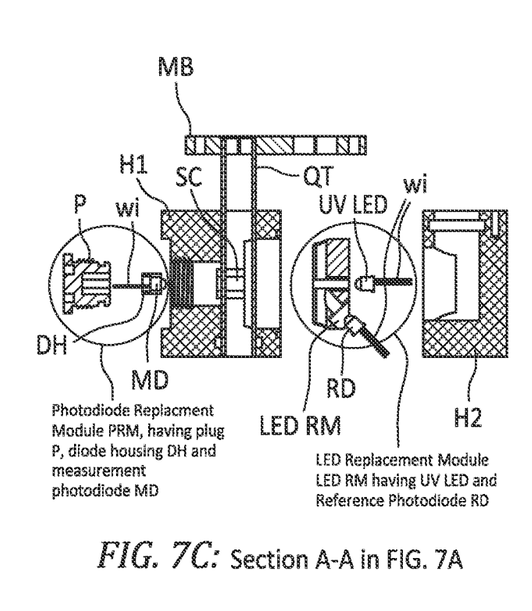
FIG. 7C is a cross-sectional view of the cell spacer in FIG. 7A along lines A-A, and where
Figure 7D:
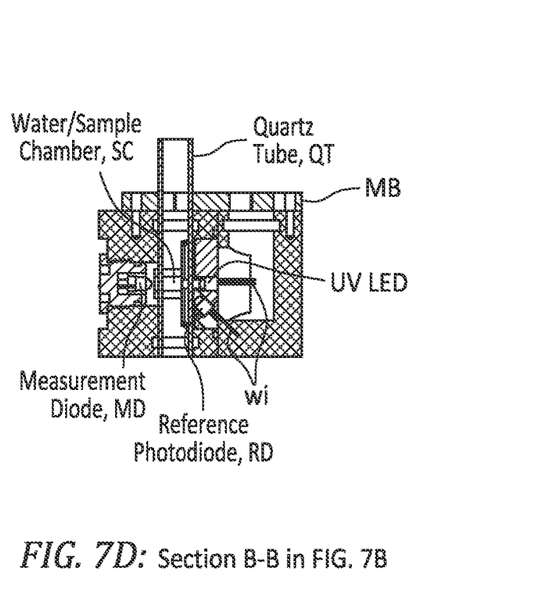
FIG. 7D is a cross-sectional view of the cell spacer in FIG. 7B along lines B-B.

For example, FIG. 6A shows a first optical sensing technique using the variable cell concept, e.g. where the first sub-chamber SC1 and the second sub-chamber part SC2 are configured to define a short path for a high concentration measurement, e.g., each sub-chamber part having a respective chamber extension CE1, CE2 with substantially the same length. The respective chamber extensions CE1, CE2 are coupled together and sealed with an O-ring O arranged inbetween. The respective chamber extensions CE1, CE2 are configured or adapted to define the short path for high concentration measurements of the water sample S. In FIG. 6A, the remaining light Lm provided from a sampling window SW arranged on one side of a sample chamber SC, passes through a first chamber window CW1, interacts with the water sample S contained within the sample chamber SC, passes through a second chamber window CW2 to a filter F arranged on the other side of the sample chamber SC, and impinges on the measurement photodiode MD. In this technique, and by way of example, since a short path for a high concentration measurement is needed, then the respective chamber extension CE1, CE2 are configured with substantially the same length and used to configured the path length for the high concentration measurement.

By way of further example, and in contrast to that shown in FIG. 6A, FIG. 6B shows a second optical sensing technique using a variable cell concept, e.g. where the first sub-chamber SC1 and the second sub-chamber part SC2' are configured to define a long path for a low concentration measurement, e.g., by each chamber extension CE1, CE2' having a substantially different length. Similar to that shown in FIG. 6A, the respective chamber extensions CE1, CE2' coupled together and sealed with an O-ring O arranged inbetween. The respective chamber extensions CE1, CE2' are arranged to define the long path for low concentration measurements of the water sample S. Similar to that shown in FIG. 6A, the remaining light Lm provided from a sampling window SW arranged on one side of a sample chamber SC interacts with the water sample S contained within the sample chamber SC, passes through a filter F arranged on the other side of the sample chamber SC, and impinges on the measurement photodiode MD. In this technique, and by way of example, since a long path for a low concentration measurement is needed, then the respective chamber extension CE1, CE2' are configured with the substantially different length and used to configured the path length for the low concentration measurement.

In FIGS. 6A and 6B, the sub-chambers SC2, SC2' includes a sample chamber leg SCL that abuts against part of the sub-chamber SC1, e.g., having a short length (FIG. 6A) or a long length (FIG. 6B) that determines the path length for the short path (FIG. 6A) or the long path (FIG. 6B).

According to some embodiments, and by way of further example, the first sub-chamber SC1 and the second sub-chamber part SC2, SC2' may also be configured to move or slide in relation to one another in order to determine or set the path length for the particular low or high concentration measurement. In this case, the respective first sub-chamber SC1 and the respective second sub-chamber part SC2, SC2' may be configured with substantially the same length, but may be slid or moved in relation to one another in order to determine a long or short path for a low or high concentration measurement, depending on the particular application.

Similar to that shown in FIG. 5, FIG. 6 shows the portion of light Lr that is sampled by a sampling window and reflected to a reference diode, e.g., like that shown in FIG. 2.

Figure 8A:
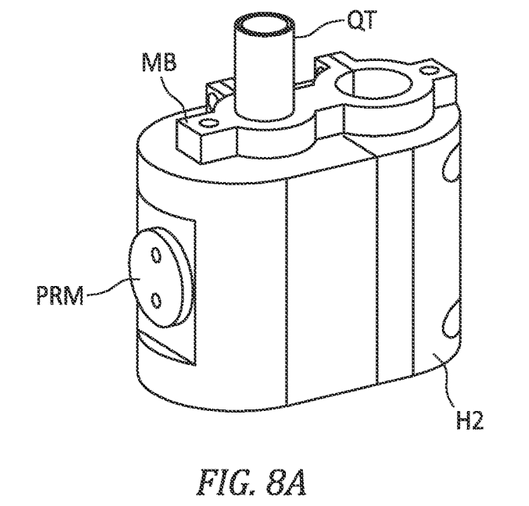
FIG. 8 includes FIGS. 8A and 8B, showing a apparatus, according to some embodiments of the present invention, where
Figure 8B:
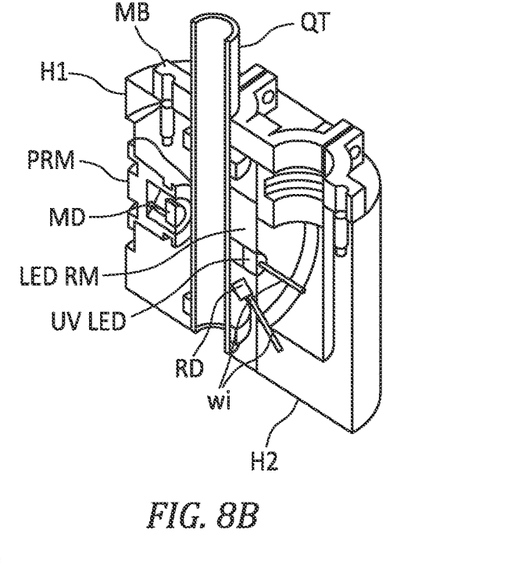
FIG. 8B is a cross-sectional view along the longitudinal axis of the apparatus in FIG. 8A.

FIGS. 7 and 8: Absorbance Module Concept

FIGS. 7 and 8 shows an embodiment, based upon using an absorbance module concept, e.g., including a photodiode replacement module PRM, having a plug P, a diode housing DH and a measurement photodiode MD arranged therein, and also including an LED replacement module LED RM, having a UV LED and a reference photodiode RD. The photodiode replacement module PRM and the LED replacement module LED RM may be configured in a housing H1 on opposite sides of a quartz tube QT (e.g., for defining a path of about 1 cm). The quartz tube QT may be configured to form a water/sample chamber SC, e.g., though which the water to be sampled passes. By way of example, the plug P of the photodiode replacement module PRM may be configured with threads for screwing into corresponding threads formed in part of the housing H1. The UV LED, the reference diode RD and measurement diode MD include associated wiring, all labeled wi, e.g., for providing suitable power and control signaling to these devices, as well as for providing suitable measured signaling back from the diodes RD and MD. A mounting bracket MB may be configured to couple the two housings H1 and H2 together, as shown.

FIG. 9

Figure 9A:
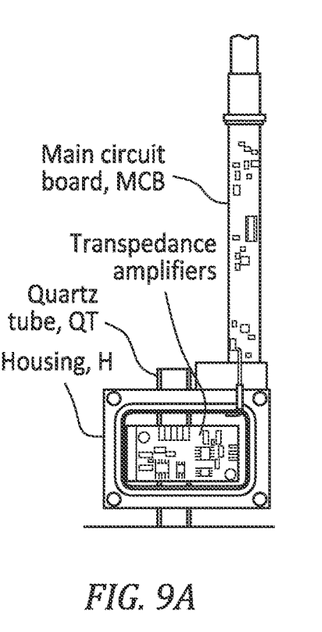
FIG. 9 includes FIGS. 9A, 9B and 9C, which show apparatus utilizing a quartz tube to define the optical path of 1 cm, according to some embodiments of the present invention.
Figures 9B, 9C:
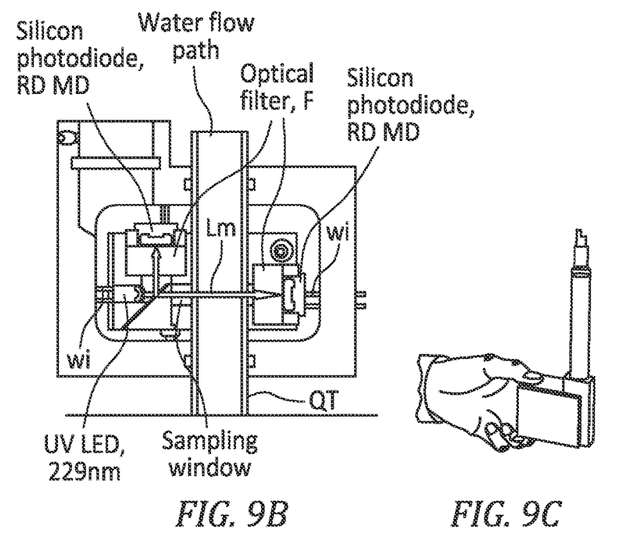

FIG. 9 shows an embodiment for optical sensing utilizing a quartz tube QT to define the optical path, e.g., of about 1 cm. FIG. 9A shows a main circuit board MCB, transimpedance amplifiers TA, the quartz tube QT and the housing H. FIG. 9B shows the water flow path WFP through the quartz tube QT, silicon photodiodes RD and MD, and optical filters F, as well as the UV LED for providing LED light at 229 nm.

Figure 10:
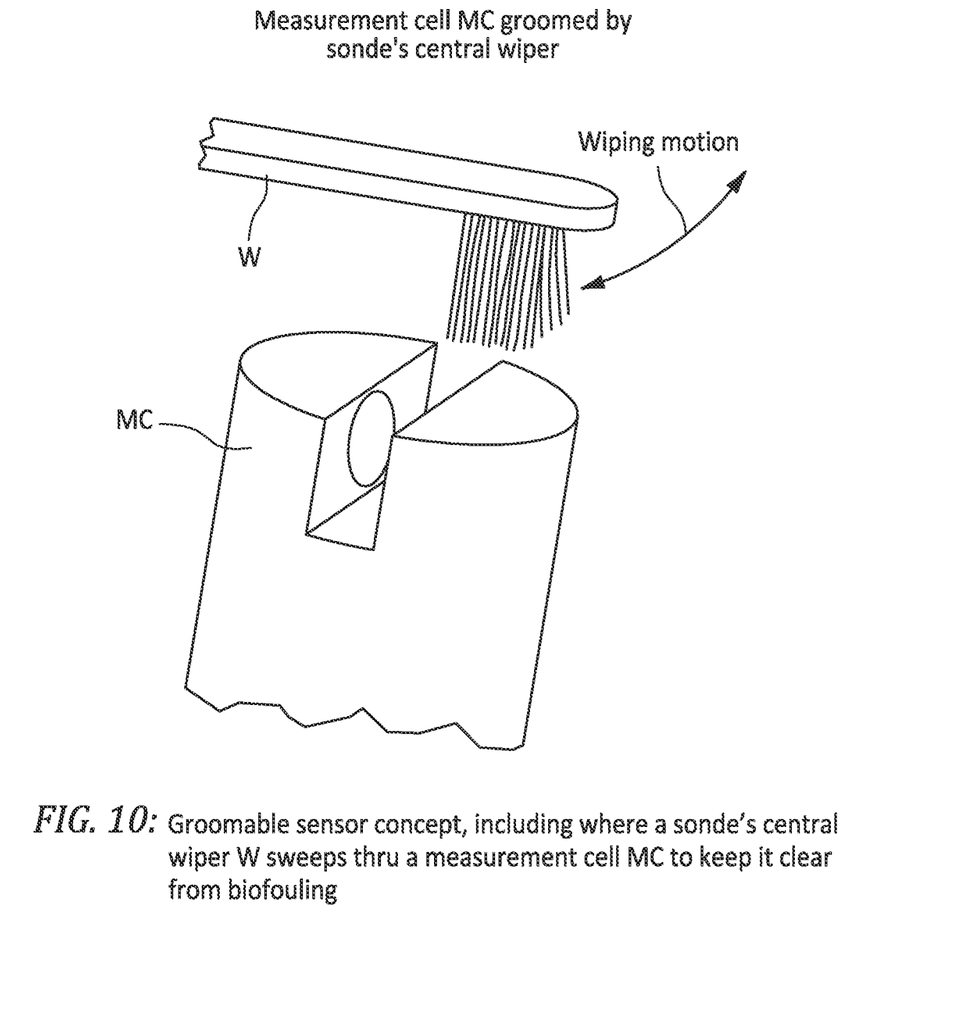
FIG. 10 is a diagram of a groomable sensor configuration, including where a sonde's central wiper sweeps thru a measurement cell to keep it clear from biofouling.

FIG. 10

FIG. 10 is a diagram of a groomable sensor concept, including where a sonde's central wiper sweeps thru a measurement cell MC to keep it clear from biofouling.

The Optical Components

By way of example, and as one skilled in the art would appreciate, optical components like LEDs, photodiodes, measurement photodiodes, reference photodiodes, optical filters, optical fiber or fibers, light pipes, LED arrays, optical sampling windows, optical pickoff windows, focusing lens, sapphire or UV grade fused silica rods, optical spectrum analyzers are all known in the art, and the scope of the invention is not intended to be limited to any particular type or kind thereof that may be used herein. The scope of the invention is intended to include using such optical components that may be now known in the art or later developed in the future.

Computer-Readable Storage Medium

According to some embodiments of the present invention, the apparatus may also take the form of a computer-readable storage medium having computer-executable components for performing the steps of the aforementioned method. The computer-readable storage medium may also include one or more of the features set forth above.

Optical Nitrate Sensor Compensation Algorithms for Multiparameter Water Quality Monitoring This application relates to the subject matter disclosed a companion patent application having Ser. No. 62/305,742 (911-023.4-1//N-YSI-0034), filed 9 Mar. 2016, entitled "Optical Nitrate Sensor Compensation Algorithms for Multiparameter Water Quality Monitoring." The optical nitrate sensor compensation algorithm disclosed in the companion application may be in conjunction with the optical nitrate sensor disclosed in the instant application, and vice versa.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. An optical nitrate sensor comprising:
a deep UV LED configured to generate a UV light centered at 229 nm that traverses a confined volume of water within a prescribed region of a sensor body;
a photodiode and transimpedance amplifier combination configured to sense a current measurement (M) of a sample portion of UV optical absorbance of nitrate concentrations dissolved in the confined volume of water of the UV light centered at 229 nm, and provide transimpedance amplifier voltage signaling containing information about a transimpedance amplifier voltage measurement (M) of the sample portion of the UV optical absorbance of the nitrate concentrations sensed;
a reference photodiode and transimpedance amplifier combination configured to sense a reference portion of the UV light centered at 229 nm not traversing the confined volume of the water, and provide reference transimpedance voltage amplifier signaling containing information about a reference transimpedance amplifier voltage measurement (R) of the reference portion of the UV light not traversing the confined volume of the water within the prescribed region of the sensor body; and
a signal processor or signal processing module configured to:
receive the transimpedance amplifier voltage signaling and the reference transimpedance voltage amplifier signaling; and
determine corresponding signaling containing information about the nitrate concentrations dissolved in the water that depends on a logarithmic relationship between the transimpedance amplifier voltage measurement (M) and the reference transimpedance amplifier voltage measurement (R), based upon the transimpedance amplifier voltage signaling and the reference transimpedance voltage amplifier signaling received.

2. An optical nitrate sensor according to claim 1, wherein the signal processor or signal processing module is configured to determine the measurement of the UV optical absorbance based upon the following equation:

Absorbance=−log(optical transmittance)=−log($M/aR$), where a is a proportionality constant that can be adjusted for electrical gain normalization.

3. An optical nitrate sensor according to claim 1, wherein the photodiode and transimpedance amplifier combination comprises
a photodiode configured to sense the UV light that is generated by the deep UV LED centered at 229 nm and traverses the confined volume of the water within the prescribed region of the sensor body, and provide photodiode signaling containing information about a measured photocurrent; and
a transimpedance amplifier configured to receive the photodiode signaling and convert the measured photocurrent into a measured voltage.

4. An optical nitrate sensor according to claim 1, wherein the reference photodiode and transimpedance amplifier combination comprises
a reference photodiode configured to sense the portion of the UV light not traversing the confined volume of the water and provide reference photodiode signaling containing information about a reference photocurrent; and
a reference transimpedance amplifier configured to receive the reference photodiode signaling, and convert the reference photocurrent into a reference voltage.

5. An optical nitrate sensor according to claim 1, wherein the UV light traverses the confined volume of the water over a varying path length that depends on a concentration range of interest for the nitrate concentration determined.

6. An optical nitrate sensor according to claim 5, wherein the sensor body comprises a variable cell configured to be adapted with a first path length for determining high concentrations of nitrate dissolved in the water, or with a second path length for determining low concentrations of nitrate dissolved in the water, including where the first path is shorter than the second path.

7. An optical nitrate sensor according to claim 1, wherein the optical nitrate sensor comprises the sensor body configured with a path length of the confined volume of the water within the prescribed region.

8. An optical nitrate sensor according to claim 7, wherein the sensor body comprises a cell spacer configured within part of the path length.

9. An optical nitrate sensor according to claim 1, wherein the signal processor or signal processing module is configured to provide the corresponding signaling containing information about the nitrate concentrations dissolved in the water.

10. An optical nitrate sensor according to claim 1, wherein the prescribed region of the sensor body comprises a sampling chamber for containing the water.

11. An optical nitrate sensor according to claim 1, wherein the optical nitrate sensor comprises a quartz tube, and the prescribed region of the sensor body forms part of the quartz tube.

12. An optical nitrate sensor according to claim 1, wherein the sensor body comprises a sonde having a sampling chamber for containing the water.

13. An optical nitrate sensor according to claim 12, wherein the sampling chamber is a two-part construction having a first sub-chamber and a second sub-chamber.

14. An optical nitrate sensor according to claim 13, wherein
the first sub-chamber includes a first sub-chamber extension;
the second sub-chamber includes a second sub-chamber extension; and
the first sub-chamber extension and the second sub-chamber extension are configured to form either a first path for a high concentration measurement or a second path for a low concentration measurement.

15. An optical nitrate sensor according to claim 14, wherein the first path for the high concentration measurement is shorter than the second path for the low concentration measurement.

16. An optical nitrate sensor according to claim 14, wherein the first sub-chamber extension and the second sub-chamber extension are coupled together and configured with an O-ring seal inbetween.

17. An optical nitrate sensor according to claim 16, wherein the first sub-chamber extension and the second sub-chamber extension are slidably coupled together.

18. An optical nitrate sensor according to claim 1, wherein
the prescribed region includes a sampling chamber; and
the optical nitrate sensor comprises the deep UV LED configured on one side of the sampling chamber, and a combination of a filter and measurement photodiode configured on the other side of the sampling chamber.

19. An optical nitrate sensor according to claim 18, wherein the optical nitrate sensor comprises one or more light pipes, each configured to channel light to or from the sampling chamber.

20. An optical nitrate sensor according to claim 1, wherein the optical nitrate sensor comprises a photodiode replacement module having a plug, a diode housing and a measurement diode arranged therein.

21. An optical nitrate sensor according to claim 1, wherein the optical nitrate sensor comprises an LED replacement module having the deep UV LED, the photodiode, the transimpedance amplifier, the reference photodiode, and the transimpedance amplifier.

22. An optical nitrate sensor according to claim 1, wherein the optical nitrate sensor is configured to provide multiparameter water quality monitoring.

23. A method comprising steps for
generating with a deep UV LED a UV light centered at 229 nm that traverses a confined volume of water within a prescribed region of a sensor body;
configuring a photodiode and transimpedance amplifier combination to sense a current measurement (M) of a sample portion of UV optical absorbance of nitrate concentrations dissolved in the confined volume of water of the UV light centered at 229 nm, and to provide transimpedance amplifier voltage signaling containing information about a transimpedance amplifier voltage measurement (M) of the sample portion of the UV optical absorbance of the nitrate concentrations sensed;
configuring a reference photodiode and transimpedance amplifier combination to sense a reference portion of the UV light centered at 229 nm not traversing the confined volume of the water, and to provide reference transimpedance voltage amplifier signaling containing information about a reference transimpedance amplifier voltage measurement (R) of the reference portion of the UV light not traversing the confined volume of the water within the prescribed region of the sensor body; and
receiving in a signal processor or processing module the transimpedance amplifier voltage signaling and the reference transimpedance voltage amplifier signaling; and
determining in the signal processor or processing module corresponding signaling containing information about the concentration of nitrate dissolved in the water that depends on a logarithmic relationship between the transimpedance amplifier voltage measurement (M) and the reference transimpedance amplifier voltage measurement (R), based upon the transimpedance amplifier voltage signaling and the reference transimpedance voltage amplifier signaling received.

24. A method according to claim 23, wherein the method comprises providing from the signal processor or signal processing module the corresponding signaling containing information about the concentration of nitrate dissolved in the water.

25. A method according to claim 23, wherein the method comprises determining with the signal processor or signal processing module the measurement of the UV optical absorbance based upon the following equation:

Absorbance=−log(optical transmittance)=−log($M/aR$), where a is a proportionality constant that can be adjusted for electrical gain normalization.

26. An optical nitrate sensor comprising:
a deep UV LED configured to generate a UV light centered at 229 nm that traverses a confined volume of water within a prescribed region of a sensor body;
a photodiode configured to sense UV optical absorbance of nitrate concentrations dissolved in the confined volume of water of the UV light centered at 229 nm, and provide sensed photodiode current signaling containing information about a current measurement of a sample portion of the UV optical absorbance of the nitrate concentrations sensed;
a transimpedance amplifier configured to receive the sensed photodiode current signaling measured, and provide transimpedance amplifier voltage signaling containing information about a transimpedance amplifier voltage measurement (M) of the UV optical absorbance of the nitrate concentrations sensed;
a reference photodiode configured to sense a reference portion of the UV light centered at 229 nm not traversing the confined volume of the water, and provide reference photodiode current signaling containing information about a reference current measurement of a reference portion of the UV light centered at 229 nm not traversing the confined volume of the water;
a reference transimpedance amplifier configured to receive the reference photodiode current signaling measured, and provide reference transimpedance voltage amplifier signaling containing information about a reference transimpedance amplifier voltage measurement (R) of the reference portion of the UV light centered at 229 nm not traversing the confined volume of the water; and
a signal processor or signal processing module configured to:
receive the transimpedance amplifier voltage signaling and the reference transimpedance voltage amplifier signaling; and
determine corresponding signaling containing information about the nitrate concentrations dissolved in the water that depends on a logarithmic relationship between the transimpedance amplifier voltage measurement (M) and the reference transimpedance amplifier voltage measurement (R), based upon the transimpedance amplifier voltage signaling and the reference transimpedance voltage amplifier signaling received.

27. An optical nitrate sensor according to claim 26, wherein the signal processor or signal processing module is configured to determine the measurement of the UV optical absorbance based upon the following equation:

Absorbance=−log(optical transmittance)=−log($M/aR$), where a is a proportionality constant that can be adjusted for electrical gain normalization.

28. An optical nitrate sensor comprising:
a signal processor or signal processing module configured to:
receive transimpedance amplifier voltage signaling containing information about a measurement of UV optical absorbance of nitrate concentrations dissolved in water of a UV light that is generated by a deep UV LED centered at 229 nm, that traverses a confined volume of the water within a prescribed region of a sensor body, that is sensed by a photodiode as a measured photocurrent, and that is provided by a transimpedance amplifier which converts the measured photocurrent into a measured transimpedance voltage (M);

receive reference transimpedance voltage amplifier signaling containing information about a reference portion of the UV light centered at 229 nm not traversing the confined volume of the water that is sampled by a reference photodiode as a reference photocurrent and provided by a reference transimpedance amplifier which converts the reference photocurrent into a reference transimpedance voltage (R); and determine corresponding signaling containing information about the nitrate concentrations dissolved in the water that depends on a logarithmic relationship between the transimpedance voltage (M) and the reference transimpedance voltage (R), based upon the transimpedance amplifier voltage signaling and the reference transimpedance voltage amplifier signaling received.

29. An optical nitrate sensor according to claim 28, wherein the signal processor or signal processing module is configured to determine the measurement of the UV optical absorbance based upon the following equation:

$$\text{Absorbance} = -\log(\text{optical transmittance}) = -\log(M/aR),$$

where a is a proportionality constant that can be adjusted for electrical gain normalization.

* * * * *